US007656538B2

(12) United States Patent
Paulus et al.

(10) Patent No.: US 7,656,538 B2
(45) Date of Patent: Feb. 2, 2010

(54) SHORT-WAVELENGTH COHERENCE TOMOGRAPHY

(75) Inventors: Gerhard Georg Paulus, Jena (DE); Christian Rödel, Max-Wien-Platz 1, Jena, Thuringia (DE) 07743

(73) Assignees: The Texas A&M University System, College Station, TX (US); Christian Rödel, Jena (DE)

( * ) Notice: Subject to any disclaimer, the term of this patent is extended or adjusted under 35 U.S.C. 154(b) by 151 days.

(21) Appl. No.: 12/038,753

(22) Filed: Feb. 27, 2008

(65) Prior Publication Data

US 2008/0212075 A1    Sep. 4, 2008

Related U.S. Application Data

(60) Provisional application No. 60/891,781, filed on Feb. 27, 2007.

(51) Int. Cl.
*G01B 11/02* (2006.01)
(52) U.S. Cl. ...... 356/497
(58) Field of Classification Search ...... 356/479, 356/497
See application file for complete search history.

(56) References Cited

U.S. PATENT DOCUMENTS

| | | | | |
|---|---|---|---|---|
| 5,451,785 A * | 9/1995 | Faris | | 250/330 |
| 5,459,570 A * | 10/1995 | Swanson et al. | | 356/479 |
| 5,921,926 A | 7/1999 | Rolland et al. | | 600/407 |
| 6,327,335 B1 | 12/2001 | Carroll | | 378/85 |
| 6,608,717 B1 * | 8/2003 | Medford et al. | | 359/368 |
| 6,618,152 B2 * | 9/2003 | Toida | | 356/479 |
| 6,999,491 B2 | 2/2006 | Rieger et al. | | 372/75 |
| 7,139,078 B2 | 11/2006 | Hogan | | 356/480 |
| 7,256,894 B2 | 8/2007 | Chen et al. | | 356/497 |
| 7,567,596 B2 * | 7/2009 | Dantus et al. | | 372/30 |

OTHER PUBLICATIONS

Bellini et al., "Temporal Coherence of Ultrashort High-Order Harmonic Pulses," *Phys. Rev. Lett.*, 81(2):297-300, 1998.
Celliers et al., "Fringe formation and coherence of a soft-x-ray laser beam illuminating a Mach-Zehnder interferometer," *Optics Letters*, 20:1907-1909, 1995.
Dromey et al., "Bright multi-keV harmonic generation from relativistically oscillating plasma surfaces," *Phys. Rev. Lett.*, 99(8):085001-085004, 2007.
Henke et al., "X-Ray Interactions: Photoabsorption, Scattering, Transmission, and Reflection at E=50-30,000 eV, Z=1-92," *Atomic Data and Nuclear Data Tables*, 54:181-342, 1993.
Huang et al., "Optical coherence tomography," *Science*, 254(5035):1178-1181, 1991.
Liu and Brezinski, "Theoretical and practical considerations on detection performance of time domain, Fourier domain, and swept source optical coherence tomography," *Journal of Biomedical Optics*, 12(4):044007, 2007.

(Continued)

*Primary Examiner*—Michael A Lyons
(74) *Attorney, Agent, or Firm*—Fulbright & Jaworski LLP (57) ABSTRACT

The present relates generally to methods, systems and apparatuses for three dimensional and cross-sectional imaging of objects (e.g., silicon) and subjects at a nanometer-scale resolution using short wave-length (e.g., extreme ultra-violet) light.

41 Claims, 8 Drawing Sheets

OTHER PUBLICATIONS

Salières and Lewenstein, "M. Generation of ultrashort coherent XUV pulses by harmonic conversion of intense laser pulses in gases : towards attosecond pulses," *Meas. Sci. Technol.*, 12(11):1818-1827, 2001.

Tsakiris et al., "Route to single attosecond pulses," *N. J. Phys.*, 8(1):2-20, 2006.
PCT International Search Report and Written Opinion, issued in International Application No. PCT/US08/55170, dated Jul. 23, 2008.

* cited by examiner

SHORT-WAVELENGTH COHERENCE TOMOGRAPHY

The present application claims the benefit of priority to U.S. Provisional Application No. 60/891,781 filed Feb. 27, 2007, the entire contents of this application being incorporated by reference.

BACKGROUND OF THE INVENTION

I. Field of the Invention

Embodiments of the present invention relate generally to methods, systems and apparatuses for three dimensional and cross-sectional imaging of objects (e.g., microstructured silicon) and subjects at high resolutions (e.g., nanometer-scale resolution) using short wave-length (e.g., extreme ultra-violet) light with an ultra-broadband spectrum.

II. Description of Related Art

Optical coherence tomography (OCT) is an interferometric, non-invasive optical tomographic imaging technique offering millimeter penetration (approximately 2-3 mm in tissue) with micrometer-scale axial and lateral resolution. OCT is a widely known imaging technique, especially in opthalmology, other biomedical applications and art conservation. The technique was first demonstrated in 1991 with ~30 μm axial resolution (Huang et al., 1991). However, OCT has not achieved a resolution much if anything below 1 μm. Such resolution would be useful for many purposes including those mentioned above, but also for imaging technical materials, such as semiconductors.

SUMMARY OF THE INVENTION

Certain shortcomings of the prior art are reduced or eliminated by methods, systems and apparatuses disclosed here. These techniques are applicable to a vast number of applications, including but not limited to any application involving three dimensional and cross-sectional imaging of objects (e.g., silicon) and subjects at high resolutions (e.g., nanometer-scale resolution). These techniques may be implemented in hardware (e.g., a system including a suitably-configured computer), software (implemented on any of a host of media known in the art), as a method, as an apparatus, or as otherwise understood by those having ordinary skill in the art. The summary below is focused on inventive techniques implemented in an apparatus, system or method, with the understanding that other analogous implementations are contemplated, such as software.

One aspect of the invention provides a tomograph comprising: (a) a femtosecond laser configured to produce a coherent ultra-intense light pulse, (b) a beam-splitter configured to split the coherent ultra-intense light pulse into a first split pulse and a second split pulse, wherein the beam splitter is also configured to vary a delay between the first split pulse and the second split pulse, (c) a focusing device configured to focus the first split pulse and the second split pulse on a high harmonic generator that converts the first split pulse and the second split pulse into a first beam and a second beam, respectively, wherein each beam is coherent, ultra-broadband, and short-wavelength, (d) a sample holder configured to hold an object or a subject in a path of the first beam to generate a first reflected beam, (e) a first reflecting device configured to reflect the second beam to produce a second reflected beam, (f) a detector in operational relation to the sample holder and the reflecting device, configured to measure interference between the first reflected beam and the second reflected beam, and (g) a processor configured to convert the measured interference into a three dimensional data set having a spatial resolution along each orthogonal axis, independently less than 500 nm.

In some embodiments, the tomographs has a spatial resolution along each orthogonal axis is from about 1 nm to about 30 nm, or from about 10 nm to about 15 nm. In further embodiments, it has a spatial resolution along the axis of the first beam (axial resolution) is from about 10 nm to about 15 nm, or about 12 nm.

In some embodiments, the tomograph has a second reflecting device configured to reflect and focus the first beam onto a object or subject held in the sample holder and a third reflecting device configured to reflect and focus the second beam onto the first reflecting device. In some of these embodiments, the second and third reflecting devices are the same.

In some embodiments, the first and the second beams can each be extreme ultraviolet (XUV) radiation, soft X-ray radiation, or X-ray radiation. In some embodiments, the coherent ultra-intense light pulse of infrared radiation or visible wavelength radiation. In some embodiments, the first split pulse and the second split pulse are configured to be parallel with respect to one another. In some embodiments, the tomograph is further configured to delay the second split pulse with respect to the first split pulse. In some embodiments, the first split pulse is configured to have a different phase than the second split pulse. In some embodiments, the first split pulse is configured to have the same phase as the second split pulse. In some embodiments, the high harmonic generator comprises a gas, for example, a gas selected from the group consisting of He, Ne, Ar, Kr, Xe, and $N_2$. In some embodiments, the high harmonic generation comprises a solid surface. In some embodiments, an imaging element is in the path of the first reflected beam. In some embodiments, the imaging element is a toroidal mirror. In some embodiments, the detector is a position sensitive detector, such as a CCD detector.

In some embodiments, the sample holder is configured to be moved parallel to the first beam, in others it is configured to be moved perpendicular to the first beam. In some embodiments, a processor is configured to convert the three dimensional data set into an image. Some embodiments further comprise an output device, such as a display.

In some embodiments, the three dimensional data set corresponds to the entire object or part of an object. In other embodiments, the three dimensional data set corresponds to the surface or sub-surface structure of the object. In some embodiments, the three dimensional data set corresponds to the surface or sub-surface structure of the object to a depth of 200 μm. In some embodiments, the object is a material comprising silicon. In some embodiments, the object is a semiconductor. In some embodiments, the object has micro- or nano-scale structural features. In some embodiments, the three dimensional data set provides spatial information corresponding to the entire subject or part of the subject. In some embodiments, the object is a biological structure. In some embodiments, the subject is a mammal, such as a human. In some embodiments, the output device is configured to store the three dimensional data set on a computer readable medium.

In another aspect of the invention, a computerized tomography method is provided having the steps: (a) obtaining an object or a subject, (b) producing a first beam and a second beam, wherein each beam is coherent and ultra-broadband, (c) irradiating the object or body with the first beam to generate a first reflected beam, (d) reflecting the second beam off a reflecting device to produce a second reflected beam, (e) generating interference at a detector between the first reflected beam and the second reflected beam, (f) measuring the interference at the detector, (g) varying a delay between the first beam and the second beam, and (h) converting the measured interference into a three dimensional data set having a spatial resolution along each orthogonal axis, independently, for example, from about 1 nm to about 30 nm. In other embodiments the spatial resolution is that of the tomograph embodiments.

In some embodiments of the method, the first and the second beams are each XUV, soft X-ray, or X-ray. In some embodiments of the method, step (b) comprises using a femtosecond laser to produce a coherent ultra-intense light pulse. In some embodiments of the method, the coherent ultra-intense light pulse is infrared or visible. In some embodiments of the method, step (b) further comprises splitting the coherent ultra-intense pulse using a beam splitter into a first split pulse and a second split pulse. In some embodiments of the method, the first split pulse and the second split pulse are parallel with respect to one another. In some embodiments of the method, the second split pulse is delayed with respect to the first split pulse. In some embodiments of the method, the first split pulse has a different phase than the second split pulse. In some embodiments of the method, the first split pulse has the same phase as the second split pulse. In some embodiments of the method, step (b) further comprises focusing the first split pulse and the second split pulse on a gas to produce the first beam and the second beam, respectively. In some embodiments of the method, the gas is selected from the group consisting of He, Ne and Ar. In other embodiments, the gas is selected from a gas selected from the group consisting of He, Ne, Ar, Kr, Xe, and $N_2$.

Some embodiments of the method further comprise moving the object or subject parallel to the first beam. Some embodiments of the method further comprise the step of converting the three dimensional data set to an image. Some embodiments of the method further comprise the step of displaying the image on an output device. In some embodiments of the method, the output device is a display. In some embodiments of the method, the three dimensional data set provides spatial information corresponding to the entire object or a part of the object. In some embodiments of the method, the three dimensional data set provides spatial information corresponding to a part of the object. In some embodiments of the method, the three dimensional data set provides spatial information corresponding to the surface or sub-surface structure of the object. In some embodiments of the method, the three dimensional data set provides spatial information corresponding the surface or sub-surface structure of the object to a depth of 200 µm. In some embodiments of the method, the object is a material comprising silicon. In some embodiments of the method, the three dimensional data set provides spatial information corresponding to the entire subject or part of the subject. In some embodiments of the method, the subject is a mammal, such as a human. Some embodiments of the method further comprise the step of storing the three dimensional data set on a computer readable medium.

Another aspect of the invention provides a tomograph comprising: (a) a femtosecond laser configured to produce a coherent ultra-intense light pulse, (b) a focusing device configured to focus the coherent ultra-intense light pulse on a high harmonic generator that converts the coherent ultra-intense light pulse into a beam, wherein the beam is coherent, ultra-broadband, and short-wavelength, (c) a sample holder configured to hold a coated object in a path of the first beam to generate a first reflected beam and a second reflected beam, (d) a detector in operational relation the sample holder, configured to measure interference between the first reflected beam and the second reflected beam, and (e) a processor configured to convert the measured interference into a three dimensional data set having a spatial resolution along each orthogonal axis, independently less than one micrometer.

The following drawings and description of illustrative embodiments, including examples and figures, are included to demonstrate specific embodiments of the invention. However, those of skill in the art should, in light of the present disclosure, appreciate that many changes can be made in the specific embodiments which are disclosed and still obtain a like or similar result without departing from the spirit and scope of the invention.

BRIEF DESCRIPTION OF THE DRAWINGS

The following drawings form part of the present specification and are included to further demonstrate certain aspects of the present invention. The invention may be better understood by reference to one of these drawings in combination with the detailed description of specific embodiments presented herein.

FIG. 1 is a schematic diagram of an embodiment of the present disclosure.

DESCRIPTION OF ILLUSTRATIVE EMBODIMENTS

I. Definitions

The use of the word "a" or "an," when used in conjunction with the term "comprising" in the claims and/or the specification may mean "one," but it is also consistent with the meaning of "one or more," "at least one," and "one or more than one."

The term "substantially," "about," and their variations are defined as being largely but not necessarily wholly what is specified as understood by one of ordinary skill in the art, and in one non-limiting embodiment, substantially refers to ranges within 10%, preferably within 5%, more preferably within 1%, and most preferably within 0.5% of what is specified.

The term "coherent" means the capability of two light beams to interfere non statistically with each other.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "extreme UV" refers to wavelengths from 5 nm to 100 nm. (Si L absorption edge 99 eV corresponds to 12.5 nm, low energy absorption edge is 20 nm and corresponds to 62 nm)

The term "infrared radiation" means radiation of a wavelength from about 700 nm to about 10,000 nm.

The term femtosecond laser means an apparatus for generating ultrashort laser pulses consisting of one to several tens of optical cycles full width at half maximum.

The term "intense femtosecond laser" means a femtosecond laser as defined above with a peak power exceeding about 10 GW and focused intensities around $10^{15}$ W/cm$^2$.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses.

The term "short-wavelength" refers to a wavelength range from extreme UV (XUV) to X-ray, including soft X-ray.

The term "soft X-ray" refers to wavelengths from about 1 nm to about 20 nm.

As used herein, the term "tomograph" means an apparatus for generating a series of tomograms, two-dimensional images of slices, sections, or cross-sections through a three-dimensional object, subject, or part thereof, which can then be converted into a three dimensional image.

The term "ultra-broadband" means a bandwidth sufficient to generate ultrashort pulses.

The term "visible wavelength radiation" means radiation of a wavelength from 400 nm to 700 nm.

The term "X-ray" refers to wavelengths from about 0.01 nm to about 1 nm.

The term "XCT" refers to coherence tomography based on XUV, soft X-ray or X-ray radiation.

II. Tomograph

Embodiments of the present invention provide, in one aspect, a tomograph capable of cross-sectional imaging of micro- and nano-structures with nanometer resolution in all three dimensions by XUV, soft X-ray or X-ray coherence tomography (XCT). In one embodiment, the tomograph is the short-wavelength (extreme ultra-violet to X-ray spectral region) version of optical coherence tomography (OCT), including frequency-domain OCT. OCT in turn is a particular variant of white-light interferometry, as described in Huang et al. (1991), which is incorporated herein by reference. In some embodiments, XCT provides for time-domain interferometry, frequency-domain interferometry, or combinations of both. As compared to conventional OCT, which provides resolutions around 5 μm, embodiments of this invention may provide resolutions on the nanometer scale due to the shorter wavelength and the broader spectral width of the radiation used.

Figure 1:
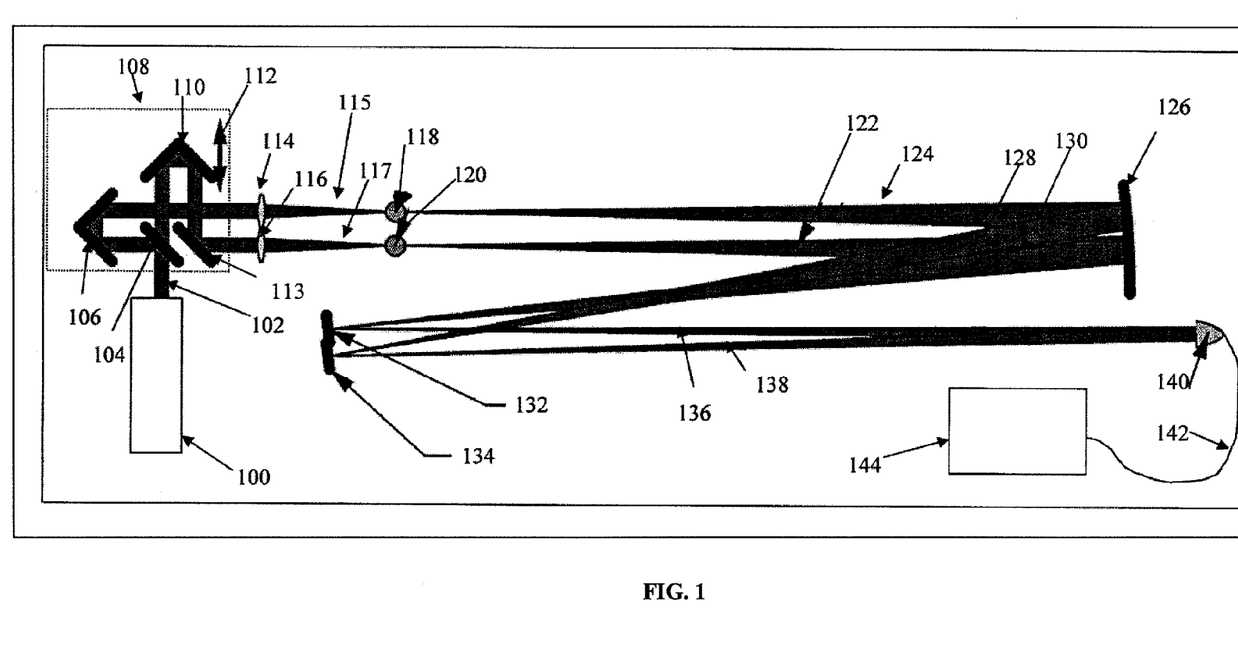
FIG. 1. Scheme of an XCT apparatus.
Figure 2:
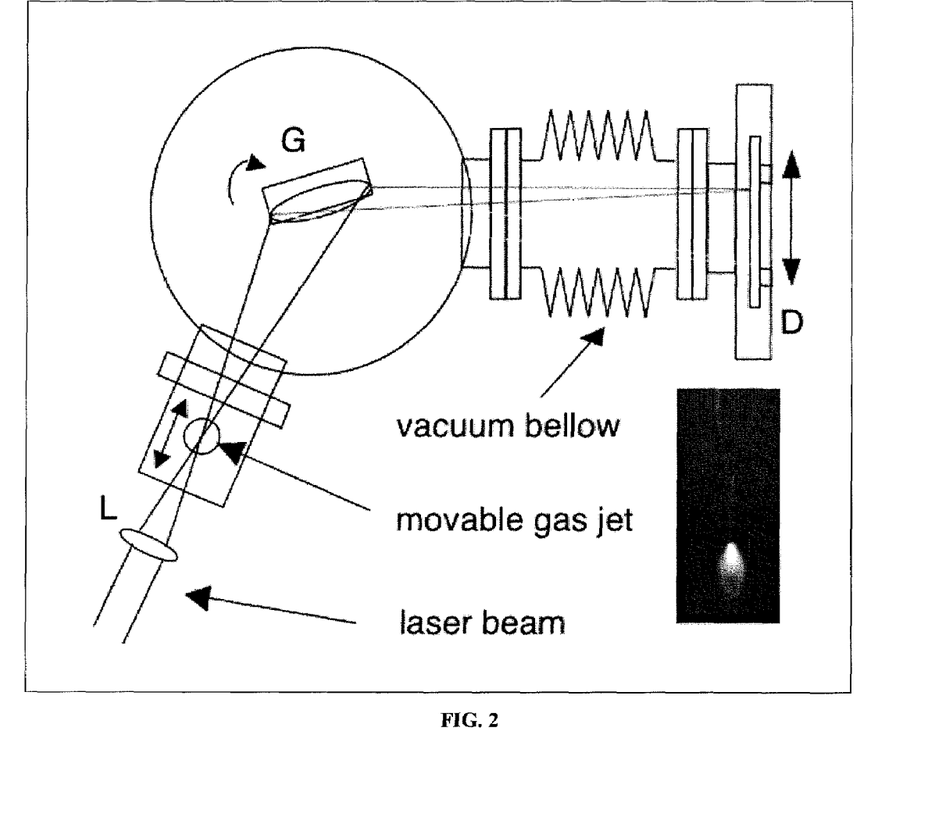
FIG. 2. Example of a setup for the generation of high harmonics in gases.

In one embodiment, two phase-coherent ultra-broadband XUV sources, beams, or pulses are generated by high-harmonic generation. For example, such sources, beams or pulses may be generated by focusing intense femtosecond laser pulses on gases or solid surfaces. An example of a possible layout of an apparatus according to one embodiment is shown in FIG. 1, discussed in greater detail below. In general, this scheme depicts the case were (i) the broadband short-wavelength radiation is generated via high-harmonic generation in gases, (ii) XCT is used in time-domain mode, (iii) the two delayed short-wavelength pulses are generated by splitting the femtosecond laser pulses. In such an embodiment, interference is detected when both XUV beams overlap at the detector within the coherence length. For ultra-broadband HHG radiation, this can be can be less than 20 nm, and which corresponds to the resolution that can be achieved (see below).

One embodiment of the present invention is shown in FIG. 1. 100 is a femtosecond laser configured to produce a coherent ultra-intense light pulse (102), which is typically visible wavelength or infrared radiation. Examples of a femtosecond lasers that may be used are, for gas harmonics, KM-Labs "Red Dragon" (http://www.kmlabs.com/laser_reddragon.htm), or for surface harmonics, Amplitude Technologies "Pulsar 200" (www.amplitude-technologies.com). Typically 102 will be a femtosecond laser beam ("fundamental") with a pulse duration depending on wavelength from about 2 to about 100 fs and a wavelength from about 300 nm to about 10 μm, and power from about 10 GW to several PW. 108 is a beam-splitter a beam-splitter configured to split the coherent ultra-intense light pulse (102) into a first split pulse (115) and a second split pulse (117). 104 is the beam-splitting part of 108. As an example, a 50% beamsplitter can be used, such as Femtolaser's OA237 (http://p52910.typo3-server.info/fileadmin/documents/Optikkatalog.pdf). 113 is high-reflecting mirror, with an angle of incidence of 45 degrees (e.g. Femtolasers VO007 HTTP://P52910.TYPO3SERVER.INFO/FILEADMIN/DOCUMENTS/OPTIKKATALOG.PDF). 106 is a roof mirror, basically two high-reflecting mirrors like item 113, but configured at 90 degrees with respect to one another. 110 is a roof mirror on or attached to a precision translation stage. Movement of 110 is typically achieved by the precision translation stage, which can, e.g., a nanoX200CAP (http://www-.piezojena.com-/index.php4?pre_cat_open=137&id=180&subid=245).

In the embodiment of FIG. 1, the first split pulse and the second split pulse are configured to be parallel with respect to one another. In other embodiments, the split pulses are not parallel. The beam splitter (108) is configured to vary a delay between the first split pulse and the second split pulse. In this embodiment, the delay is varied by moving reflecting device 110 along the directions indicated by the double-headed arrow 112. In some embodiments, 110 may be a mirror. In some embodiments, different cross-sections of a sample can be recorded by delaying the first and the second split pulse with respect to each other.

Taken together 114 and 116 in the embodiment shown in FIG. 1, is a focusing device configured to focus the first split pulse (115) and the second split pulse (117), respectively. In this embodiment, the focusing device is shown as two distinct units that are near to one another. In other embodiments, the two units may be further separated from one another. A will be understood by a person skilled in the art, 114 and 116 can vary depending on the type of laser used. For example, for gas harmonics with focal length >1000 mm, an achromatic lens would typically be used (e.g., Thorlabs "AC-508-1000-C"). For surface harmonics of ultrabroadband femtosecond laser pulses concave mirrors would typically be used as focusing devices.

In the embodiment of FIG. 1, the first split pulse (115) and the second split pulse (117) are focused on 118 and 120, respectively. 118 and 120 each represent a high harmonic generator, which is a device for frequency upconversion. In this embodiment, the high harmonic generator is shown as two distinct units that are near to one another. In other embodiments, the two units may be further separated from one another. In further embodiments, the focusing device may be one unit. In the embodiment of FIG. 1, the high harmonic generator (118 and 120 taken together) that converts the first split pulse (115) and the second split pulse (117) into a first beam (124) and a second beam (122), respectively. Typically, 122 and 124 are mutually coherent and mutually delayed XUV, soft X-ray, or X-ray beams. In the embodiment shown in FIG. 1 (gas harmonics), the high harmonic generator comprises a gas. Typically, the gas will be selected from the group consisting of He, Ne, Ar, Kr, Xe, and $N_2$. For example, Ne at 10 mbar can be used. (see Salières and Lewenstein, 2001). In other embodiments, such as surface harmonics, the high harmonic generation comprises a solid surface, such as a glass plate (see Dromey et al., 2007). Typically 118 and 120, each also include a filter selecting the required bandwidth of short-wavelength radiation.

In the embodiment of FIG. 1, 126 is a second reflecting device configured to reflect and focus the first beam (124) onto a object or subject held in sample holder 134. For example, 126 can be a focusing mirror, such as a toroidal mirror. 124 (also known as the probe beam) is the first beam before it has been reflected and focused, and 128 is the first beam after it has been reflected and focused. In the embodiment shown in FIG. 1, 126 is also a third reflecting device configured to reflect and focus the second beam (122) onto the first reflecting device (132). Similarly, 122 is the second beam (also known as a reference beam) before it has been reflected and focused, and 130 is the first beam after it has been reflected and focused. As shown in FIG. 1, the second and third reflecting devices may be one unit. In other embodiments, they may be more than one unit.

134 is a sample holder configured to hold an object or a subject in a path of the first beam (128) to generate a first reflected beam (138). 132 is the first reflecting device and is configured to reflect the second beam (130) to produce a second reflected beam (136). Typically 132 is a mirror with a reflectance approximately matching that of the sample. In some embodiments, the sample 134 holder is configured to be moved parallel to the first beam (128) and/or perpendicular to the first beam. Parallel movement of 134 can be used to allow different cross-sections of an object or a subject to be recorded. Perpendicular movement of 134 allows for a cross section image to be recorded. Furthermore, in some embodiments, cross-sectional imaging can be achieved by changing the direction of the first beam or by moving the sample parallel to the surface. Such movement can be combined to produce a three dimensional data set. In some embodiments, Furthermore, cross-sectional imaging can be achieved by scanning the sample slightly changing the direction of the XUV beam or by moving the sample parallel to the surface.

140 is a detector in operational relation to the sample holder 134 and the reflecting device 132. 134: mirror with a reflectance approximately matching that of the sample. The detector is configured to measure interference between the first reflected beam (138) (e.g., radiation reflected from an object, sample or subject) and the second reflected beam (136) (e.g., reflected radiation from the first reflecting device). In the embodiment of FIG. 1, interference is detected when both beams overlap at the detector within the coherence length. Typically for ultra-broadband HHG radiation, this can be considerably shorter than 20 nm. A typical X-ray detector that can be used to measure this interference is Princeton Instruments back-illuminated CCD "PIXIS-XO". This detector allows imaging a cross section without laterally scanning the sample relative to the probe beam if an imaging element (not shown) (e.g. a toroidal mirror) is used between 132, 134 and 140. In the embodiment of FIG. 1, XCT is used in time-domain mode, 142 shows a connection between detector 140 and processor and/or output device 144. Typically such a connection is provide by a cable or wireless network, each configured to transfer data.

For gas harmonics, items 118-140 are typically situated in a vacuum apparatus, with a background gas pressure of 6-10 mbar. Typically the region where the gas is situated must be separated from the rest of the vacuum apparatus by a differential pumping stage. For surface harmonics, items 114-140 are typically situated in a vacuum apparatus. For tomographs employing soft X-rays vacuum may not be required.

In the embodiments showing in FIG. 1, 144 represents a processor. In other embodiments, it may also represent an output device, such as a display (e.g., a monitor). Processor 144 is configured to convert the measured interference into a three dimensional data set. Examples of processors that can be used with this invention include a data acquisition system, e.g. a PC together with a PC card controlling the detector. In certain embodiments, the processor further configured to convert the three dimensional data set into an image. In other embodiments, a separate one or more additional processor(s) is used to convert the image.

Figure 3:
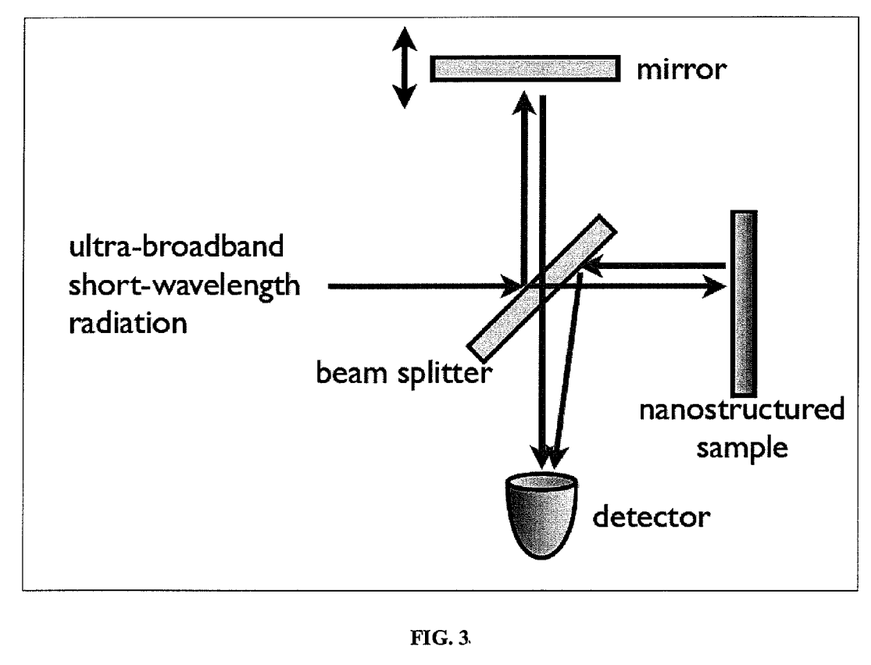
FIG. 3. Delay-stage for XCT based on X-ray optics.

In one embodiment, a pair of beams is generated by splitting a femtosecond (fs) laser beam with a beam splitter and a delay stage with which both pulses can be delayed with respect to each other. An example of such a set up is shown in FIG. 3.

In some frequency-domain OCT embodiments, a single beam and no delay stage may be sufficient for the simplest variant of the tomography. See, for example, FIG. 5 for one such embodiment shown in FIG. 5. In this embodiment, the XUV radiation is recombined onto the sample under investigation and the resulting interferences in the scattered radiation are recorded on a detector in dependence of all three orthogonal directions. In this embodiment, the case of certain frequency-OCT embodiments, varying the delay is optional, however, the detection of the scattered light has to be done by a spectrometer.

In other embodiments, XCT can also be realized for ultrathin samples in transmission.

Image reconstruction from the data has been described extensively in the literature. See Liu and Brezinski, 2007, which is incorporated herein by reference.

III. Resolution

The axial resolution (i.e. perpendicular to the surface of the sample and parallel to the short-wavelength beam) is given by the coherence length $\lambda_c \approx 0.5\lambda^2/\Delta\lambda$ assuming a Gaussian spectrum, where $\lambda$ is the central wavelength of the white-light source and $\Delta\lambda$ the FWHM bandwidth. The lateral resolution is given by the wavelength and the numerical aperture. Therefore, the shorter the wavelength and the bigger the bandwidth, the higher the resolution. (Using fs-lasers or superradiant diodes, conventional OCT achieves axial resolutions down to 5 μm.)

High-harmonic generation in gases can efficiently produce coherent XUV radiation up to at least 100 eV photon energy and has the potential of 10 nm resolution in some embodiments.

High-harmonic generation on solid surfaces is capable of providing intense coherent broadband radiation with much greater efficiency at much shorter wavelengths and correspondingly broader bandwidth. Recent research has shown efficient production of harmonics up to several keV photon energy. See, for example, Dromey et al. (2007), which is incorporated herein by reference. As the same physical laws apply for calculating the resolution, sub-nanometer resolutions are possible. However, in some embodiments the resolution will be limited by the mechanical precision of the apparatus rather than limitations given by the laws of optics.

In some embodiments, where the source (e.g., a split pulse) is XUV radiation the methods, apparatuses, or systems of the invention provide a range of resolutions that can be achieved from about 10 nm to about 200 nm. In other embodiments, the bottom end of the resolution range is 1 nm, 12 nm, 13 nm, 14 nm, 15 nm, 20 nm, 25 nm, 30 nm, 35 nm, 40 nm, or 50 nm. For certain embodiments, the top end of the resolution range is 50 nm, 60 nm, 75 nm, 90 nm, 100 nm, or 200 nm.

In some embodiments, where the source (e.g., a split pulse) is soft-X-Ray radiation the methods, apparatuses, or systems of the invention provide a range of resolutions that can be achieved from 1 nm to 100 nm. In other embodiments, the bottom end of the resolution range is 5 nm, 6 nm, 7 nm, 8 nm, 9 nm, 10 nm, 11 nm, 12 nm, 13 nm, 14 nm, 15 nm, or 20 nm. For certain embodiments, the top end of the resolution range is 20 nm, 25 nm, 30 nm, 35 nm, 40 nm, 50 nm, 60 nm, 75 nm, 90 nm, or 95 nm.

In some embodiments, where the source (e.g., a split pulse) is X-Ray radiation the methods, apparatuses, or systems of the invention provide a range of resolutions that can be achieved from 1 nm to 100 nm. In other embodiments, the bottom end of the resolution range is 1 nm, 2 nm, 3 nm, 4 nm, or 5 nm. For certain embodiments, the top end of the resolution range is 20 nm, 25 nm, 30 nm, 35 nm, 40 nm, 50 nm, 60 nm, 75 nm, 90 nm, or 95 nm.

IV. Femtosecond Laser

XCT pulses consisting of as few as possible optical cycles may provide an advantage in certain embodiments of the invention. Accordingly, one may choose to use few-cycle pulses. The term femtosecond laser means an apparatus for generating ultrashort laser pulses consisting of one to several tens of optical cycles full width at half maximum. The term intense femtosecond laser means a femtosecond laser as defined above with a peak power exceeding 10 GW and focused intensities around $10^{15}$ W/cm$^2$. Such powers can be achieved by systems generating pulses with 1 mJ energy and 100 fs or shorter pulse duration. Several companies offer systems with pulse energies exceeding 10 mJ and pulse durations below 25 fs. Such lasers have pulse repetition rates on the order of 1 kHz. They are well-suited for generation of gas harmonics.

For surface harmonic generation, femtosecond lasers with peak powers exceeding 10 TW may be necessary. Surface harmonics are generated when the TW femtosecond pulse creates a plasma on the surface and the electrons oscillate with relativistic velocities. This calls for intensities exceeding $10^{19}$ W/cm$^2$. Respective laser systems are commercially available, most notably by Amplitude (France) and Thales (France). Pulse energies exceed 1 J and the pulse duration varies between 20 and 100 fs. The pulse repetition rate for the present state-of-the-art is 10 Hz. Alternatives are even larger systems with PW power (very low repetition rate) or few-cycle lasers.

V. High-Harmonic Generation (HHG)

In one aspect, XCT requires (at least) two mutually delayed pulses of broadband short-wavelength radiation. In other embodiments, XCT can require more than two such pulses. In certain embodiments, pulses of broadband short-wavelength radiation can be achieved by high-order frequency up-conversion (high-harmonic generation, HHG) of intense femtosecond laser pulses. The femtosecond laser radiation is also referred to as the fundamental. Two non-limiting embodiments are described here. Both have the advantage of not only providing broadband short-wavelength radiation. Rather, the radiation is coherent in addition, in particular also with respect to the fundamental. While coherent laser-like radiation is not mandatory for XCT in principle, it is very useful for certain embodiments, as this allows circumventing a pulse splitter and delay stage for the short-wavelength radiation.

A. HHG in Gases—Gas Harmonics

When intense laser pulses are focused on diluted gases (pressure≈1 to 10 mbar), harmonics of the fundamental are emitted. See, for example, Salières and Lewenstein (2001), which is incorporated herein by reference. Depending on the intensity and the wavelength of the fundamental, harmonics up to an order of several hundred can be generated. The photon energy (in units of eV) of the highest harmonics is given by $0.3I\lambda^2+E_{ion}$, where I is the intensity in units of W/cm$^2$, $\lambda$ the wavelength in meters, and $E_{ion}$ the ionization energy of the gas atoms. The equation is valid as long as the gas atoms are not close to being fully ionized. This limits intensities to ≈$10^{15}$ W/cm$^2$ unless ions can be used.

Efficiency of HHG in gases depends on the focusing geometry because it is limited by phase matching. Quasi-phase matching techniques affect the bandwidth achievable thus reducing axial resolution. Broader bandwidth at reduced efficiencies can be realized by focusing the femtosecond radiation onto the gas with a long focal length f. Then, the efficiency scales roughly like f$^3$. Lasers with high pulse energy can achieve efficiencies of ≈$10^{-5}$ at 40 eV photon energy. See Salières and Lewenstein (2001) for an example of a harmonic spectrum generated by intense femtosecond pulses focused on neon gas.

B. HHG on Solid Surfaces—Surface Harmonics

An intense laser pulse interacting with a solid surface will ionize the atoms at the surface and thus generate a plasma at the surface. The free electrons of the plasma reflect the incident light. The laser produces the mirror for its own reflection. For sufficiently intense laser pulses (>$10^{19}$ W/cm$^2$), the electrons in the plasma will oscillate at relativistic velocities. Therefore, the reflected light will be strongly modulated, i.e. new frequencies—the surface harmonics—are generated. See, for example, Tsakiris et al. (2006), which is incorporated herein by reference. Tsakiris et al. (2006) includes a figure showing a typical setup for the generation of high harmonics at solid surfaces. A harmonic spectrum generated by intense femtosecond pulses focused on a solid surface is shown by Dromey et al. (2007).

Surface harmonic generation is a perfectly coherent process of extraordinarily high efficiency (several percent as compared to $10^{-5}$ for gas harmonics). In addition, and in contrast to gas harmonics, there is no known intensity limit. The harmonics are generated by the already fully ionized medium (the plasma), whereas gas harmonics are generated by atoms during the ionization process. The disadvantages are tied to the present state of laser technology, including high demands on the laser system used. Pulses of extremely high intensity (>$10^{19}$ W/cm$^2$) and pulse quality are needed in many cases. Pulse quality refers to pulse contrast: Typically prepulses will be at least about 10 orders of magnitude less intense than the main pulse to avoid premature plasma formation. In addition, keeping optical aberrations small helps achieve higher intensities. However, tremendous progress has been made in the past years in this respect and such lasers are commercially available today, for example from Amplitude Technologies (France), "Pulsar 200", a 250-TW laser system (www.amplitude-technologies.com).

VI. Pulse Splitter and Delay Stage

Variations of OCT, including XCT, are based on correlating light scattered at the sample with light of a coherent reference beam. Scattered and reference beam have a mutual delay. The delay is variable in the case of time-domain XCT. The two coherent short-wavelength beams can be realized in different ways for different aspects of this invention.

For example, in certain embodiments, analogous to OCT, the short-wavelength can be split by a beamsplitter. One of the split beams is sent to the sample, the other to a mirror. The light scattered at the mirror and the sample is recombined and detected by a photodiode or by a spectrometer. See FIG. 3 for an example of such a set up. Schemes in transmission are also possible. The disadvantage of the scheme is that optical elements (mirrors, beamsplitters, etc.) at XUV, soft-X-ray, and X-ray wavelength are expensive and often inefficient.

Figure 4:
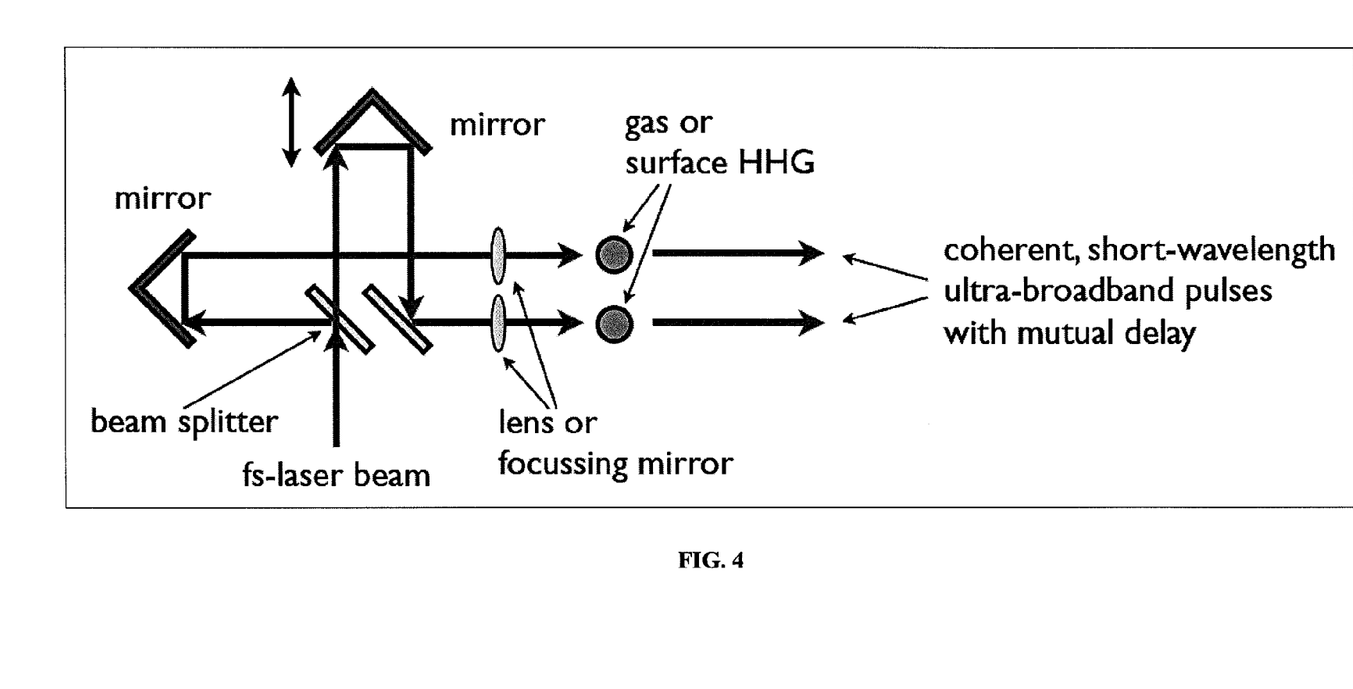
FIG. 4. Delay-stage for XCT based on generating two coherent beams of ultra-broadband short-wavelength radiation.

It is known that HHG in gases and at surfaces not only provides a source of ultra-broadband short-wavelength radiation with comparatively high brightness. In addition, this radiation is also coherent with respect to the fundamental. This implies that two short-wavelength beams generated in this way by the same fundamental will also be mutually coherent. For gas harmonics this has been shown. See, for example, Bellini et al. (1998), which is incorporated herein by reference. For surface harmonics this follows from theory. The mutual coherence of the two beams can be used to bypass cumbersome X-ray optics to a large degree. The delay stage is set up for the femtosecond pulses, see FIG. 4.

In a further embodiment, an even simpler implementation of XCT can be achieved by coating the nanostructured sample with a thin layer (thickness on the order of the coherence length). See FIG. 5 for an example of such a tomograph comprising. 500 is the a femtosecond laser. 502 is a coherent ultra-intense light pulse. 514 is a focusing device configured to focus the coherent ultra-intense light pulse on a high harmonic generator (518) that converts the coherent ultra-intense light pulse into a beam (522), wherein the beam is coherent, ultra-broadband, and short-wavelength. 532 is a sample holder configured to hold a coated object in a path of the first beam to generate a first reflected beam (536) and a second reflected beam (538). 540 is a detector in operational relation the sample holder, configured to measure interference between the first reflected beam and the second reflected beam. 544 is a processor configured to convert the measured interference into a three dimensional data set having a spatial resolution along each orthogonal axis, independently less than one micrometer.

Figure 5:
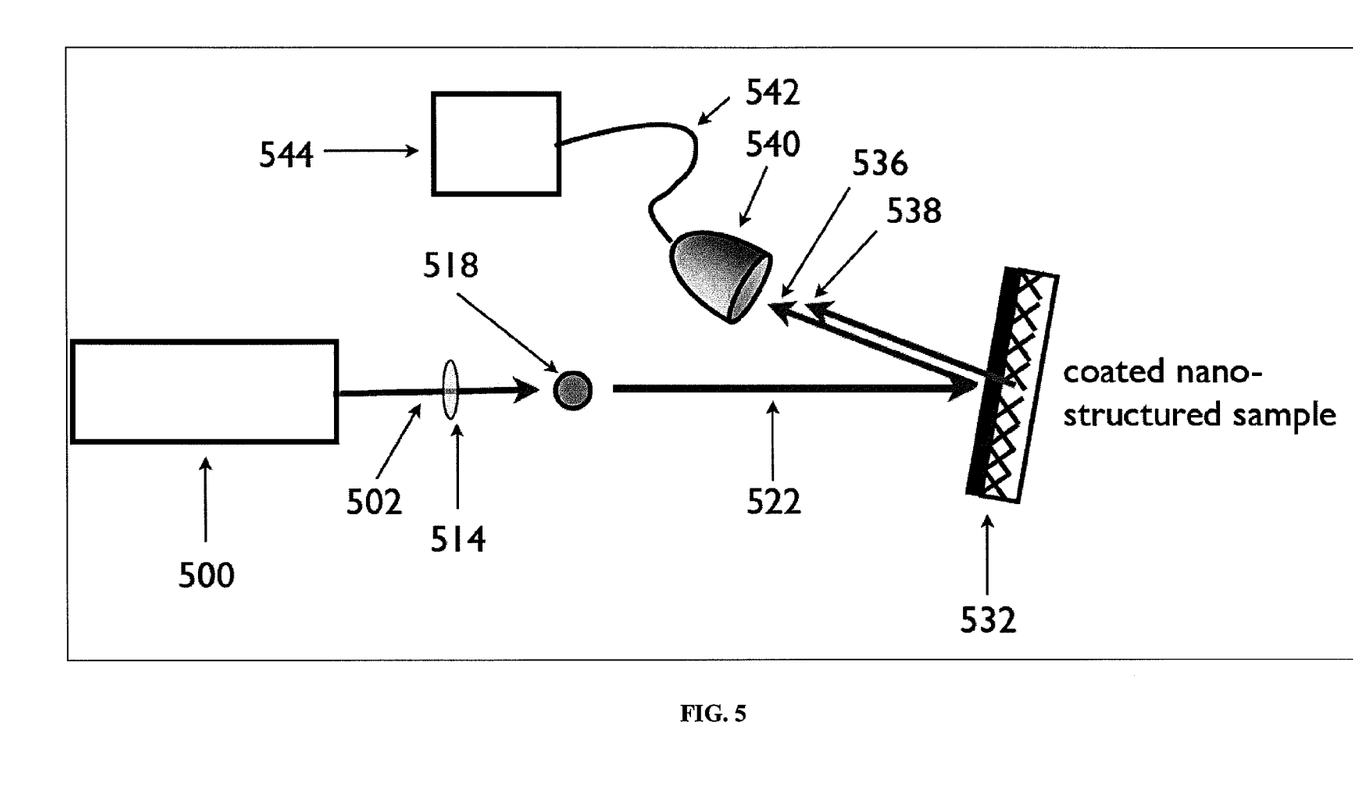
FIG. 5. Version of a frequency-domain XCT. The delay stage is realized by a thin coating of the sample.

For example, the following elements can be used: 500: Femtosecond laser: For gas harmonics e.g. KM-Labs "Red Dragon" (HTTP://WWW.KMLABS.COM/LASER_RED-DRAGON.HTM), For surface harmonics e.g. Amplitude Technologies "PULSAR 200" (HTTP://WWW.AMPLI-TUDE-TECHNOLOGIES.COM/) 502: Femtosecond laser beam ("fundamental"). Pulse duration: depending on wavelength about 2 to 100 fs. Wavelength: about 300 nm to 10 µm. Power 10 GW to several PW. 514: Focusing element: Depending on the laser used an achromatic lens (for gas harmonics focal length >1000 mm, e.g. Thorlabs "AC-508-1000-C", for surface harmonics of ultrabroadband femtosecond laser pulses typically concave mirrors) 518: device for frequency upconversion: for gas harmonics target gas (e.g. Ne 10 mbar) (see Salieres et al.), for surface harmonics glass plate (see Dromey et al). 118, 120 also include a filter selecting the required bandwidth of short-wavelength radiation. 536: reflected radiation from sample 538: reflected radiation from front- or rearside of the thin film; 540: X-ray detector: e.g. Princeton Instruments back-illuminated CCD "PIXIS-XO" (This detector allows imaging a cross section without laterally scanning the sample relative to the probe beam if an imaging element (e.g. a toroidal mirror) is used between 518 and 540—full-field XCT (Please use that term also in the caption of FIG. 1 and the claim that I have added.); 542: cable to the data acquisition system; 544: data acquisition system, e.g. a PC together with a PC card controlling the detector.

The coating is expected to act as a beam splitter for the XUV radiation and via its thickness as a delay stage at the same time. However, the delay can not be changed. Therefore, this method works for frequency-domain XCT only. The deposition of thin (nanometer of micrometer thickness) films on samples is mature technology used in many areas of science and technology. In general, thin films are thin material layers ranging from fractions of a nanometer to several micrometers in thickness. There exists a large variety of methods for thin-film deposition suitable for virtually all kinds of materials. For the present purpose it is important to select the material of the thin film such that the intensities reflected on the thin film and on/in the sample itself are of the same order of magnitude in order to achieve a sufficient contrast of the resulting interference pattern. The selection will depend on the material of the sample as well as on the wavelength used.

VII. Application to Silicon and Related Materials

In principle, XCT faces similar difficulties as OCT arising from absorption. On the other hand, HHG covers a much broader spectral range than available in the optical regime (Salières and Lewenstein, 2001). Further progress in HHG will increase flexibility even more once significant XUV intensity is available at several hundred eV. The invention contemplates that it will be possible to find a wavelength band allowing 200 nm or deeper penetration for many technologically interesting materials. See below.

Figure 6:
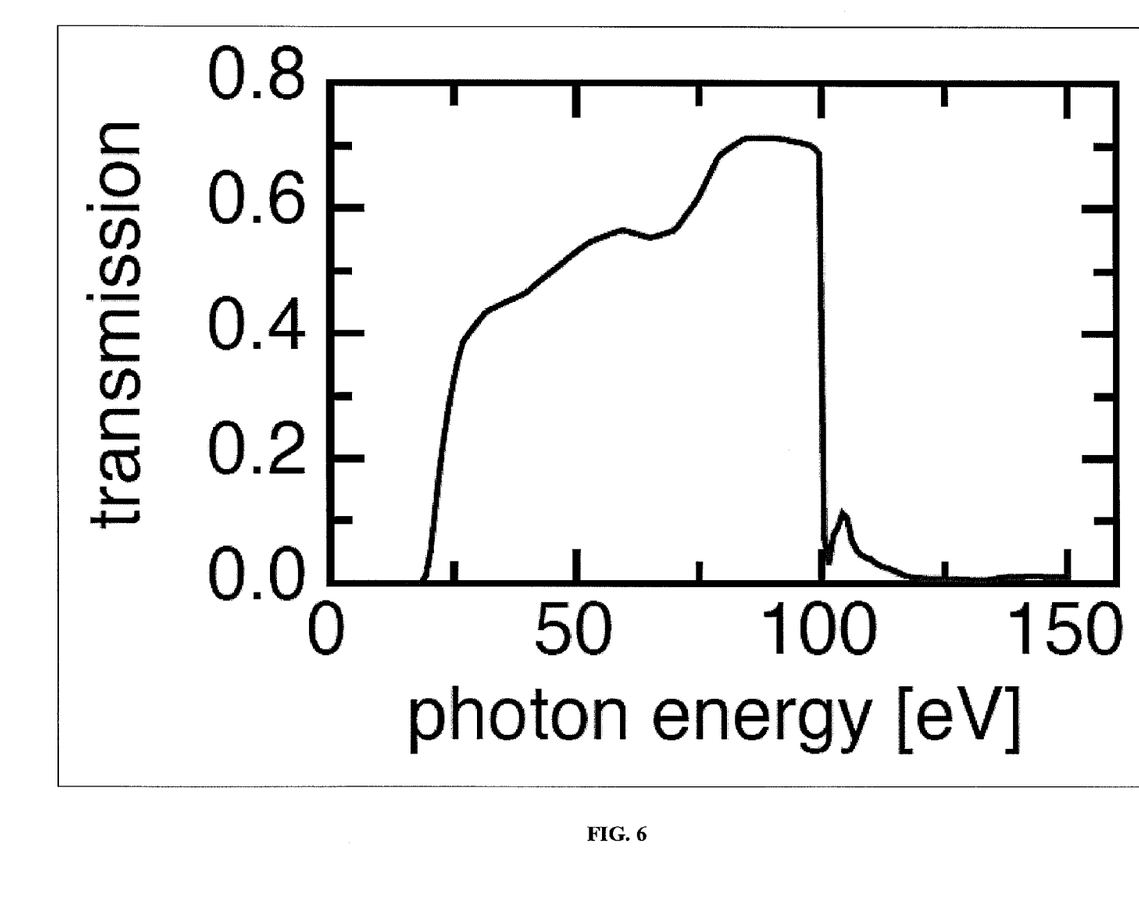
FIG. 6. Transmission of XUV radiation through a 200-nm thick silicon plate.

In certain embodiments, the techniques, apparatuses and systems of this invention can be applied to the three-dimensional or cross sectional imaging of silicon, or silicon-related materials, including using readily available HHG sources. In general silicon offers more than 200 nm penetration for radiation having a wavelength between 20 and 60 nm (see FIG. 6). In certain embodiments, this corresponds to an axial resolution for nanostructures embedded in Si of around 20 nm. Any structures, doping, etc. with other material will lead to a very high contrast because most other atoms absorb very strongly in this wavelength domain. Typically strong absorption leads to high refraction indices, which can lead to reflection at boundaries of silicon with other embedded material(s).

Generating 10-µJ XUV pulses in the XUV via harmonic generation in gases is known (see Salières and Lewenstein, 2001). Surface harmonics can provide similar levels of pulse energy in the soft X-ray and X-ray regime (see Dromey et al., 2007). As an example a bilayer structure of silicon (Si) and molybdenum (Mo) is considered. Detecting and measuring the Mo embedded in Si can be achieved via the method depicted in FIG. 5.

The reflectivity in the XUV is $>10^{-4}$. Thus, the reflected energy is >1 nJ which has to be detected by a detector, say a spectrometer. The spectrometer efficiency is composed of the transmission of its XUV filter ($\cong 0.6$), efficiency of a light-collecting toroidal mirror ($\cong 0.8$), grating efficiency ($\cong 0.1$), and the efficiency of the CCD ($\cong 0.2$). I.e. the efficiency of the spectrometer is about 1%. It is then straightforward to calculate that there will be $\cong 10^6$ photons per pulse in the CCD which can be detected readily.

Figure 7:
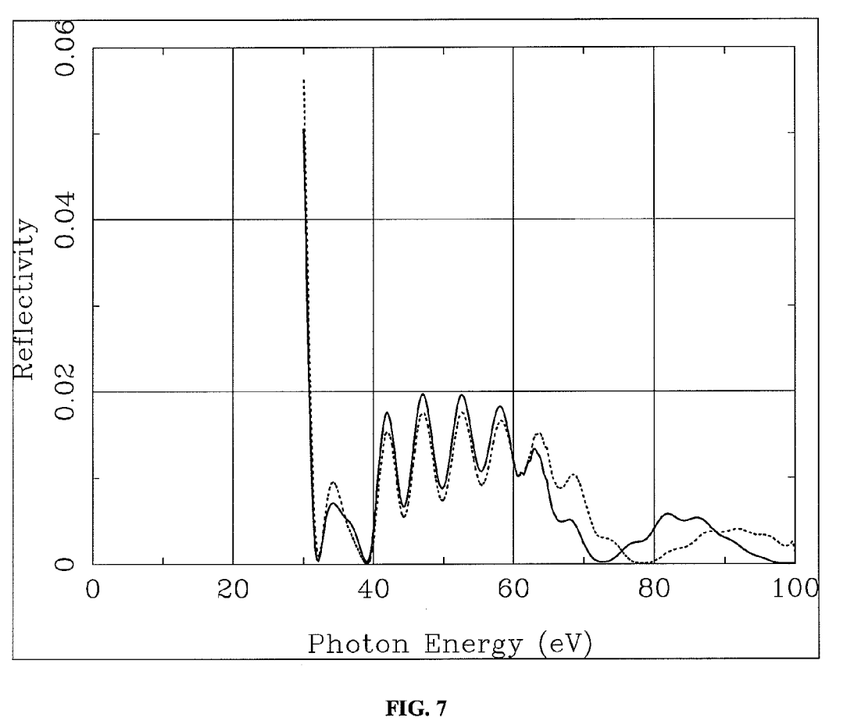
FIG. 7. Reflectivity dependence on photon energy for a silicon (Si) and molybdenum (Mo) bilayer sample on a Si substrate. The solid line corresponds to 100 nm Si, 20 nm Mo layer; the dashed line corresponds to 100 nm Si, 18 nm Mo layer.
Figure 8:
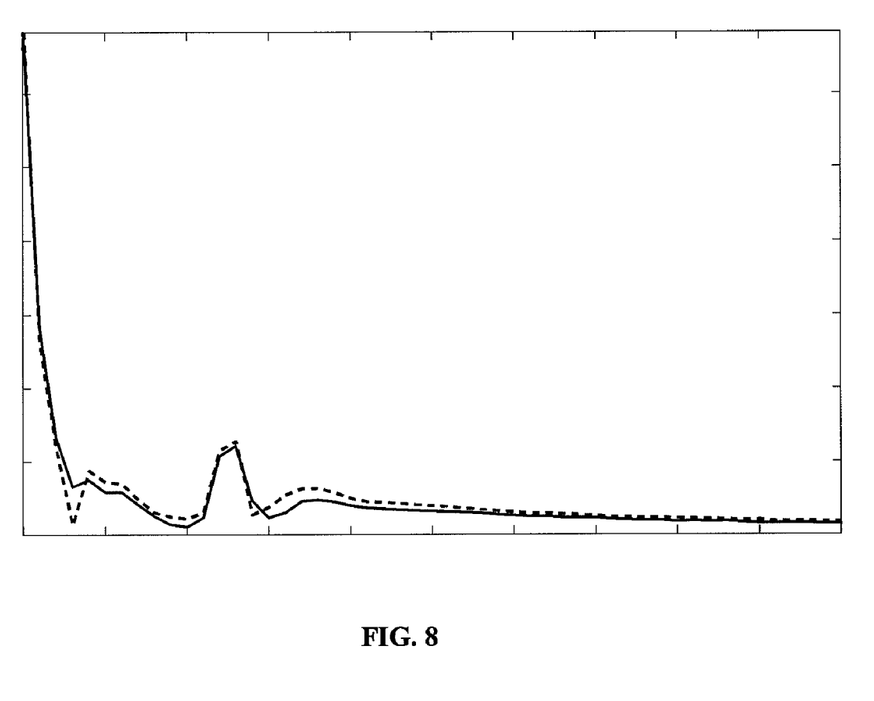
FIG. 8. Fast Fourier transform of the sample of FIG. 7. The peak at scale unit 2 to 3 of the X-axis corresponds to the Mo layer (solid line 20 nm, dashed line 18 nm).

FIGS. 7 & 8 show the dependence of reflected radiation on photon energy for a 100-nm Si layer covering a 20 nm and 18 nm Mo layer on a Si substrate. The graphs were calculated using the matrix layer algorithm of reference 6 (Henke et al). Although the 2-nm difference in layer thickness is small as compared to the theoretical limit of resolution ($\approx 12$ nm), the differences are already noticeable and become readily detectable for larger differences in thickness.

VIII. Application to Biological Structures and Subjects

The methods, apparatuses and systems of the present invention can also, in other aspects of the invention be applied to three-dimensional or cross-sectional imaging of biological materials, subjects or patients. For example, XCT can be applied to biological samples. One example is cross-sectional imaging in the so-called water window (2.3 to 4.4 nm), i.e. the spectral region where water is transparent but carbon absorbs strongly. This property will lead to high contrast lateral resolution with soft x-rays. The present state of technology suggests that coherent (and bright) radiation in this spectral domain can be generated most efficiently by surface harmonic generation.

All of the methods, systems and apparatuses disclosed and claimed herein can be made and executed without undue experimentation in light of the present disclosure. While the methods, systems and apparatuses of this invention have been described in terms of specific examples, it will be apparent to those of skill in the art that variations may be applied to the methods, systems and apparatuses described herein without departing from the concept, spirit and scope of the invention. All such modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bellini et al., *Phys. Rev. Lett.*, 81(2):297-300, 1998.
Celliers et al., *Optics Lett.*, 20:1907-1909, 1995.
Dromey et al., *Phys. Rev. Lett.*, 99(8):085001-4, 2007.
Henke et al., *Atomic Data And Nuclear Data Tables*, 54:181-342, 1993.
Huang et al., *Science*, 254(5035):1178-1181, 1991.
Liu and Brezinski, *J. Biomed. Optics* 12(4), 2007
Salières and Lewenstein, *Meas. Sci. Technol.*, 12(11):1818-1827, 2001.
Tsakiris et al., *N. J. Phys.*, 8(1):2-20, 2006.

What is claimed is:

1. A tomograph comprising:
   (a) a femtosecond laser configured to produce a coherent ultra-intense light pulse;
   (b) a beam-splitter configured to split the coherent ultra-intense light pulse into a first split pulse and a second split pulse, wherein the beam splitter is also configured to vary a delay between the first split pulse and the second split pulse;
   (c) a focusing device configured to focus the first split pulse and the second split pulse on a high harmonic generator that converts the first split pulse and the second split pulse into a first beam and a second beam, respectively, wherein each beam is coherent, ultra-broadband, and short-wavelength;
   (d) a sample holder configured to hold an object or a subject in a path of the first beam to generate a first reflected beam;
   (e) a first reflecting device configured to reflect the second beam to produce a second reflected beam;
   (f) a detector in operational relation the sample holder and the reflecting device, configured to measure interference between the first reflected beam and the second reflected beam; and
   (g) a processor configured to convert the measured interference into a three dimensional data set having a spatial resolution along each orthogonal axis, independently less than 500 nm.

2. The tomograph of claim 1, wherein the spatial resolution along each orthogonal axis is from about 1 nm to about 30 nm.

3. The tomograph of claim 1, wherein the spatial resolution along the beam axis is from about 10 nm to about 15 nm.

4. The tomograph of claim 1, wherein the spatial resolution along the axis of the first beam (axial resolution) is from about 10 nm to about 15 nm.

5. The tomograph of claim 1, wherein the spatial resolution along the axis of the first beam (axial resolution) is about 12 nm.

6. The tomograph of claim 1, further comprising a second reflecting device configured to reflect and focus the first beam onto a object or subject held in the sample holder and a third reflecting device configured to reflect and focus the second beam onto the first reflecting device.

7. The tomograph of claim 6, wherein the second and third reflecting devices are the same.

8. The tomograph of claim 1, wherein the first and the second beams are each of extreme ultraviolet (XUV) radiation.

9. The tomograph of claim 1, wherein the first and the second beams are each of soft X-ray radiation.

10. The tomograph of claim 1, wherein the first and the second beams are each of X-ray radiation.

11. The tomograph of claim 1, wherein the coherent ultra-intense light pulse of infrared radiation.

12. The tomograph of claim 1, wherein the coherent ultra-intense light pulse is of visible wavelength radiation.

13. The tomograph of claim 1, wherein the first split pulse and the second split pulse are configured to be parallel with respect to one another.

14. The tomograph of claim 1, further configured to delay the second split pulse with respect to the first split pulse.

15. The tomograph of claim 1, wherein the first split pulse is configured to have a different phase than the second split pulse.

16. The tomograph of claim 1, wherein the first split pulse is configured to have the same phase as the second split pulse.

17. The tomograph of claim 1, wherein the high harmonic generator comprises a gas.

18. The tomograph of claim 17, wherein the gas is selected from the group consisting of He, Ne, Ar, Kr, Xe, and $N_2$.

19. The tomograph of claim 17, wherein the high harmonic generation comprises a solid surface.

20. The tomograph of claim 1, further comprising an imaging element in the path of the first reflected beam.

21. The tomograph of claim 20, wherein the imaging element is a toroidal mirror.

22. The tomograph of claim 1, wherein the detector is a position sensitive detector.

23. The tomograph of claim 22, wherein the position sensitive detector is a CCD detector.

24. The tomograph of claim 1, wherein the sample holder is configured to be moved parallel to the first beam.

25. The tomograph of claim 1, wherein the sample holder is configured to be moved perpendicular to the first beam.

26. The tomograph of claim 1, further comprising a processor configured to convert the three dimensional data set into an image.

27. The tomograph of claim 1, further comprising an output device.

28. The tomograph of claim 27, wherein the output device is a display.

29. The tomograph of claim 27, wherein the output device is configured to store the three dimensional data set on a computer readable medium.

30. The tomograph of claim 1, wherein the three dimensional data set corresponds to the entire object.

31. The tomograph of claim 30, wherein the three dimensional data set corresponds to a part of the object.

32. The tomograph of claim 1, wherein the three dimensional data set corresponds to the surface or sub-surface structure of the object.

33. The tomograph of claim 32, wherein the three dimensional data set corresponds to the surface or sub-surface structure of the object to a depth of 200 µm.

34. The tomograph of claim 1, wherein the object is a material comprising silicon.

35. The tomograph of claim 1, wherein the object is a semi-conductor.

36. The tomograph of claim 1, wherein the object has micro- or nano-scale structural features.

37. The tomograph of claim 1, wherein the three dimensional data set provides spatial information corresponding to the entire subject or part of the subject.

38. The tomograph of claim 1, wherein the object is a biological structure.

39. The tomograph of claim 1, wherein the subject is a mammal.

40. The tomograph of claim 39, wherein the mammal is a human.

41. A tomograph comprising:
(a) a femtosecond laser configured to produce a coherent ultra-intense light pulse;
(b) a focusing device configured to focus the coherent ultra-intense light pulse on a high harmonic generator that converts the coherent ultra-intense light pulse into a beam, wherein the beam is coherent, ultra-broadband, and short-wavelength;
(c) a sample holder configured to hold a coated object in a path of the first beam to generate a first reflected beam and a second reflected beam;
(d) a detector in operational relation the sample holder, configured to measure interference between the first reflected beam and the second reflected beam; and
(e) a processor configured to convert the measured interference into a three dimensional data set having a spatial resolution along each orthogonal axis, independently less than one micrometer.

* * * * *